(12) United States Patent
Nichamin

(10) Patent No.: US 9,788,994 B2
(45) Date of Patent: Oct. 17, 2017

(54) EYE TREATMENT

(71) Applicant: Louis D. Nichamin, Avon, CO (US)

(72) Inventor: Louis D. Nichamin, Avon, CO (US)

(*) Notice: Subject to any disclaimer, the term of this patent is extended or adjusted under 35 U.S.C. 154(b) by 0 days.

(21) Appl. No.: 15/135,354

(22) Filed: Apr. 21, 2016

(65) Prior Publication Data

US 2016/0235585 A1    Aug. 18, 2016

Related U.S. Application Data

(62) Division of application No. 13/992,768, filed as application No. PCT/US2011/067479 on Dec. 28, 2011, now abandoned.

(60) Provisional application No. 61/428,043, filed on Dec. 29, 2010.

(51) Int. Cl.
| | |
|---|---|
| *A61K 36/61* | (2006.01) |
| *A61F 9/00* | (2006.01) |
| *A61K 9/00* | (2006.01) |
| *A61K 36/82* | (2006.01) |
| *A61M 37/00* | (2006.01) |

(52) U.S. Cl.
CPC .............. *A61F 9/0008* (2013.01); *A61F 9/00* (2013.01); *A61K 9/0048* (2013.01); *A61K 36/61* (2013.01); *A61K 36/82* (2013.01); *A61M 2037/0007* (2013.01)

(58) Field of Classification Search
CPC ...................................................... A61K 36/61
USPC ........................................................ 424/769
See application file for complete search history.

(56) References Cited

U.S. PATENT DOCUMENTS

| | | | |
|---|---|---|---|
| 4,778,457 A | | 10/1988 | York |
| 9,095,566 B1 | * | 8/2015 | Yavitz .................... A61K 33/38 |
| 2002/0169461 A1 | | 11/2002 | Simon et al. |
| 2003/0092776 A1 | | 5/2003 | Ron et al. |
| 2004/0092959 A1 | | 5/2004 | Bernaz |
| 2004/0243275 A1 | | 12/2004 | Goldman |
| 2005/0037034 A1 | | 2/2005 | Rhoades |
| 2005/0069566 A1 | | 3/2005 | Tamarkin et al. |

(Continued)

FOREIGN PATENT DOCUMENTS

| | | |
|---|---|---|
| JP | H6-56650 | 3/1994 |
| JP | 2007531767 | 11/2007 |

(Continued)

OTHER PUBLICATIONS

Afonso et al.; Correlation of Tear Fluorescein Clearance and Schimer test Scores with Ocular Irritation Symptoms; Ophthalmol; 106(4):803-810; Apr. 1999.

(Continued)

*Primary Examiner* — Chris R Tate
(74) *Attorney, Agent, or Firm* — Shay Glenn LLP

(57) ABSTRACT

Methods and kits for treating or preventing an eye condition or for cleaning an eye area tissue are provided. A method of the invention includes administering an isoprenoidal essential oil to eye area tissue, chafing eye area tissue with an abrasive, and removing the abrasive. A kit according to the invention includes an isoprenoidal essential oil, an abrasive for chafing eye area tissue, and in instruction for use for treating an eye condition or cleansing an eye area tissue. The invention also includes a composition of matter comprising an isoprenoidal essential oil and a plurality of abrasive particles in ophthamologically acceptable base.

21 Claims, 6 Drawing Sheets

(56) References Cited

U.S. PATENT DOCUMENTS

| | | |
|---|---|---|
| 2005/0220742 A1 | 10/2005 | Breen |
| 2006/0264497 A1 | 11/2006 | Zeligs |
| 2007/0203462 A1 | 8/2007 | Soroudi |
| 2008/0032605 A1 | 2/2008 | Chan |
| 2008/0131470 A1 | 6/2008 | Witham et al. |
| 2008/0166307 A1 | 7/2008 | Fontana et al. |
| 2008/0206155 A1 | 8/2008 | Tamarkin et al. |
| 2009/0061025 A1 | 3/2009 | Gao et al. |
| 2009/0093421 A1 | 4/2009 | Kaoukhov et al. |
| 2009/0137533 A1 | 5/2009 | Adkins |
| 2009/0138026 A1 | 5/2009 | Wu |
| 2009/0214676 A1* | 8/2009 | Gao ............... A61K 36/23 424/725 |
| 2010/0129465 A1 | 5/2010 | Blotsky et al. |
| 2010/0273870 A1* | 10/2010 | Gao ............... A61K 31/35 514/456 |
| 2010/0285155 A1 | 11/2010 | Gilbard et al. |
| 2011/0212157 A1 | 9/2011 | Edelson et al. |
| 2011/0300241 A1 | 12/2011 | Hsu |
| 2012/0004320 A1* | 1/2012 | Gao ............... A61K 36/23 514/729 |
| 2012/0014883 A1 | 1/2012 | Scott et al. |
| 2013/0184693 A1 | 7/2013 | Neev |
| 2013/0224272 A1* | 8/2013 | Gao ............... A61K 31/35 424/402 |
| 2013/0331768 A1 | 12/2013 | Nichamin |
| 2013/0344128 A1* | 12/2013 | Gao ............... A61K 36/23 424/443 |

FOREIGN PATENT DOCUMENTS

| | | |
|---|---|---|
| JP | 2008-133197 | 6/2008 |
| JP | 2009533454 | 9/2009 |
| JP | 2010509220 | 3/2010 |
| WO | WO 2006/119174 A1 | 11/2006 |

OTHER PUBLICATIONS

Aroni et al.; Rosacea: A Clinicopathological approach; Dermatol; 209 (3):177-182; Mar. 2004.

Baima et al.; Demodicidosis Revisited; Acta Derm Venereol; 82(1):3-6; Jan. 2002.

Bassett et al.; A comparative study of tea-tree oil versus benzoylperoxide in the treatment of acne; (Abstract); Med J Aust; 153(8):455-458; Oct. 1990.

Biju et al.; Tea tree oil concentration in follicular casts after topical delivery: determination by high-performance thin layer chromatography using a perfused bovine udder model (Abstract); J Pharm Sci; 94(2):240-245; Feb. 2005.

Bonnar et al.; The Demodex Mite Population in Rosacea; Dermatol; 28 (3):443-448; Mar. 1993.

Caldefie-Chezet et al.; Anti-inflammatory effects of Melaleuca alternifolia essential oil on human polymorphonuclear neutrophils and monocytes; Free Radio Res; 38(8):805-811; Aug. 2004.

Carson et al.; Safety, efficacy and provenance of tea tree (*Melaleuca alternifolia*) oil; Contact Dermatitis; 45(2):65-67; Aug. 2004.

Cross et al.; Human skin penetration of the major components of Australian tea tree oil applied in its pure form and as a 20% solution in vitro; (Abstract); Eur J Pharm Biopharm; 69(1):214-222; May 2008.

Dalton, M.; Demodex Treatment Options; Eyeworld (http://www.eyeworld.org/article.php?sid=4381); pp. 1-4; printed Nov. 20, 2009.

Di Pascuale et al.; Clinical Characteristics of Conjunctivochalasis with or without Aqueous Tear Deficiency; Br J Ophthalmol; 88(3):388-392; Mar. 2004.

Edwards-Jones et al.; The effect of essential oils on methicillin-resistant *Staphylococcus aureus* using a dressing model; Burns; 30(8):772-777; Dec. 2004.

Enshaieh et al.; The efficacy of 5% topical tea tree oil gel in mild to moderate acne vulgaris: A randomized, double-blind placebo-controlled study; http://www.ijdvl.com/article.asp?issn=0378-6323;year=2007;volume=73;issue=1;spage=22;epage=25;aulast=Enshaieh; pp. 1-8; printed May 31, 2011.

Forton et al.; Density of Demodex folliculorum in rosacea: a case-control study using standardized skin-surface biopsy; Br J Dermatol; 128(6):650-659; Jun. 1993.

Forton et al.; Demodicosis and rosacea: epidemiology and significance in daily dermatologic practice; J Am Acad Dermatol; 52(1):7487; Jan. 2005.

Gao et al.; Clinical Treatment of Ocular Demodecosis by Lid Scrub With Tea Tree Oil; Cornea; 26(2):136-143; Nov. 2005.

Gao et al.; High Prevalence of Demodex in Eyelashes with Cylindrical Dandruff; Invest Ophthalmol Vis Sci; 46(9):3089-3094; Sep. 2005.

Gao et al.; In vitro and in vivo killing of ocular Demodex by tea tree oil; Br J Ophthalmol; 89(11):1468-1473; Nov. 2005.

Gupta et al.; Role of Antifungal Agents in the Treatment of Seborrheic Dermatitis; Am J Clin Dermatol; 5(6):417-422; Dec. 2004.

Halcon et al.; *Staphylococcus aureus* and wounds: A Review of Tea Tree Oil as a Promising Antimicrobial; Am J Infect Control; 32:402-408; Nov. 2004.

Hammer et al.; Antifungal effects of *Melaleuca alternifolia* (tea tree) oil and its components on Candida albicans, Candida glabrata and *Saccharomyces cerevisiae*; J Antimicrob Chemother; 53(6):1081-1085; Jun. 2004.

Kheirkhah et al.; Corneal manifestations of ocular demodex infestation (Abstract); Am J Ophthalmol; 143(5):743-749; May 2007.

Kheirkhah et al.; Fluorescein dye improves microscopic evaluation and counting of Demodex in blepharitis with cylindrical dandruff; Cornea; 26:697-700; Jul. 2007.

Kuhnigk et al.; *Bacillus oleronius* sp.nov., a member of the hindgut flora of the termite Reticulitermes santonensis (Feytaud); Can J Microbiol; 41(8):699-706; Aug. 1995.

Lacey et al.; Mite-related bacterial antigens stimulate inflammatory cells in rosacea; Br J Dermatol; 157(3):474R481; Sep. 2007.

Li et al.; Correlation Between Ocular Demodex Infestation and Serum Immunoreactivity to Bacillus Proteins in Patients with Facial Rosacea; Ophthalmology; 117:870-877; May 2010.

Meller et al.; Conjunctivochalasis: Literature Review and Possible Pathophysiology; Surv Ophthalmol; 43(3):225-232; Nov.-Dec. 1998.

Messager et al.; Assessment of the antibacterial activity of tea tree oil using the European EN 1276 and EN 12054 standard suspension tests; J Hosp Infect; 59(2):113-125; Feb. 2005.

Nordqvist; What Is Rosacea? What Causes Rosacea?; Medical News Today; pp. 1-8; Aug. 11, 2009.

O'Connor, A.; Remedies: Tea Tree Oil for Acne; http://well.blogs.nytimes.com/2011/01/27/remedies-tea-tree-oil-for-acne/; pp. 1-2; printed May 31, 2011.

Oliva et al.; Antimycotic Activity of Melaleuca Alternifolia Essential Oil and Its Major Component; Lett Appl Microbiol; 37:185-187; Aug. 2003.

Powell F.C.; Clinical practice. Rosacea; N Engl J Med; 352(8):793-803; Feb. 2004.

Powell F.C.; What's Going on in Rosacea; J Eur Acad Dermatol Venereol; 14(5):351-352; Sep. 2004.

Prabhasawat et al.; Frequent Association of Delayed Tear Clearance in Ocular Irritation; Br J Ophthalmol; 82(6):666-675; Jun. 1998.

Roque et al.; Demodicosis: Treatment & Medication; http://emedicine.medscape.com/article/1203895-treatment; pp. 1-3; printed Nov. 23, 2009.

Sheha et al.; Demodex Blepharitis: Diagnosis and Treatment; http://www.osref.org/demodex-blephartis.aspx; pp. 1-3; printed Nov. 19, 2009.

Wilkin et al.; Standard grading system for rosacea: Report of the National Roaacea Society Expert Committee on the Classification and Staging of Rosacea; J Am Acad Dermatol; 50(6):907-912; Jun. 2004.

(56) References Cited

OTHER PUBLICATIONS

Wilkin J.K.; Oral thermal-induced flushing in erythematotelangiectatic rosacea; J Invest Dermatol; 76:15R18; Jan. 1981.

* cited by examiner

EYE TREATMENT

CROSS REFERENCE TO RELATED APPLICATIONS

This application is a division of U.S. application Ser. No. 13/992,768, filed Aug. 26, 2013, which is the national stage of International Application No. PCT/US2011/067479, filed Dec. 28, 2011, which application claims the benefit under 35 U.S.C. 119 of U.S. Provisional Application No. 61/428,043, filed Dec. 29, 2010, all of which are herein incorporated by reference.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention pertains to methods and kits for treating and preventing eye and body conditions and for cleaning eye area tissue. The invention also pertains to a composition of matter usable by the methods and kits.

BACKGROUND

Problems in and around the eyelid can be caused by various diseases or conditions. Causes include seborrheic dermatitis (dandruff), the presence of a bacterial infection (commonly *Staphylococcus*), a blocked oil gland in the eyelid, food, pollen or other allergies, and ocular rosacea.

Eyelid problems can result in blepharitis, which is an inflammation, often chronic, of the eyelid. Blepharitis is one of the most common eye disorders. Blepharitis can occur in two regions of the eye: at the lid margin on the outside front part of the eyelid where the eyelashes grow (referred to as "anterior blepharitis") and at the inner eyelid where the moist part of the eyelid contacts the eye and the meibomian (oil) glands are located (referred to as "posterior blepharitis"). Symptoms of blepharitis can include a red, itchy, irritated and/or swollen eyelid, crusting of the eyelid upon awakening, a sensation of a foreign body in the eye, a sensation of burning in the eye, sensitivity of the eye to light, and/or loss of eyelashes.

Ocular rosacea is a condition that affects the eyelids and ocular surface. Ocular rosacea is a long term, inflammatory eye disease that can cause blepharitis and, less commonly, conjunctivitis (inflammation or infection of the conjunctiva that lines the eyelid and part of the eyeball). The presence of ocular rosacea is commonly characterized by irritation, dryness, redness in the eyes, grittiness in the eyes, and/or blurry vision. In more severe cases of ocular rosacea, lid margin and conjunctival telangiectasias (appearance of blood vessels near the surface), eyelid crusts, eyelid scales, corneal infiltrates, corneal ulcers, vascularization, and on occasion, sight-threatening disease occur.

By some estimates, appearance of ocular rosacea correlates with the presence of facial rosacea about 50% of the time. Facial rosacea is a chronic skin condition involving abnormality in the sebaceous glands of the face and eyelids. Facial rosacea occurs on the forehead, cheeks, and nose and is divided into several subtypes, erythematotelangiectatic rosacea (characterized by redness, flushing, and telangiectasias, which is appearance of small blood vessels); papulopustular rosacea, (characterized by small bumps and pus filled lesions-including the presence of papules which are elevations of the skin without fluid) and pustules which are small, inflamed, pus filled, blister like lesions on the skin surface); and phymatous rosacea (characterized by thickened, bumpy skin).

Facial rosacea can affect anyone, but commonly starts in a person after about age 30, and preferentially affects individuals with light colored skin. Facial rosacea is widespread, with an estimated 10% of the American population exhibiting symptoms.

The exact cause(s) of facial and/or ocular rosacea are not known. Cold or windy weather, genetic factors, hot baths, infection with the bacteria *Helicobacter pylori* (commonly associated with the presence of stomach ulcers), side effects of certain medications, ingestion of hot or spicy foods or drinks, stress, sun exposure, and the presence of *Demodex folliculorum* or *Demodex brevis* on the skin of the face and/or eyelid have been proposed as possible causes or triggers for rosacea.

The arthropod *Demodex* is a tiny ectoparasitic mite that lives in or near skin, hair and eyelash follicles of mammals, including humans. The two species *D. folliculorum* and *D. brevis* can co-exist in the face and eyelids, although *D. brevis* in particular tends to burrow into the eyelash sebaceous glands and the meibomian glands, where it lays eggs. Larvae hatch after about 4 days, and take another seven days to develop into adults. The lifespan of a mite is several weeks. Some data suggest that *Demodex* mites may harbor the bacterium *Bacillus oleronius*. One mechanism that has been hypothesized to explain how the presence of *Demodex* might correlate with rosacea is that the human immune system responds to proteins produced by *B. oleronius*, resulting in inflammation (see, e.g., Li et al., "Correlation between ocular *Demodex* infestation and serum immunoreactivity to *Bacillus* proteins in patients with facial rosacea", *Ophthalmology* 2010; 117:870-877 and references therein).

Although sometimes referred to as "acne rosacea" and confused with acne vulgaris (referred to commonly as "acne") because both cause irritation to the face, facial rosacea and acne are different, and therefore the treatments recommended to manage them are also different.

Acne is the most common skin condition in the United States. While it can occur at any age, it most commonly affects teenagers and young adults. Facial rosacea is distinguished from acne vulgaris by the presence of non-inflammatory comedones (follicles filled with sebum and sloughed off cells; commonly referred to as "whiteheads" and "blackheads") with acne and their absence in facial rosacea.

Although acne and rosacea sometimes co-exist in skin, they often occur do not overlap and dermatologists recommend different protocols for treatment of rosacea and acne. The goals with acne treatments are to reduce oil production, speed up skin turnover, control bacterial infection and reduce inflammation. In addition to cleansing the skin, acne may be treated with application of acetone, alcohol, antibiotics, astringents, benzoyl peroxide, retinoids and salicylic acid, and/or ingestion of oral antibiotics, and, for women, ingestion of oral contraceptives. Techniques that cause exfoliation, such as chemical peels and microdermabrasion, may be used.

The effects of acne may be reduced but not eliminated by applying a sufficient amount of tea tree oil. Enshaieh et al. (*Indian J. Dermatol Venereol Leprol.* 2007, January-February: 73(1):22-25) describe the difficulties of obtaining an acne treatment medicine that has an effect and is tolerated by patients. Enshaieh et al. report use of 5% tea tree oil to treat mild to moderate acne vulgaris and found that 5% tea tree oil was 3.55 times more effective in improving total acne lesions and 5.75 times more effective in reducing acne severity as measured by the Acne Severity Index (ASI). Bassett et al. (*Med J Aus*), 1990 Oct. 15, 153(8):455-8 examined the effectiveness of 5% tea tree oil in reducing the number of inflamed and non-inflamed lesions in patients with acne. Application of 5% tea tree oil for twenty minutes two times a day for 45 minutes to patients suffering from acne reduced the number of lesions. The tea tree oil acted more slowly than the acne treatment (benzoyl peroxide) to which it was compared. Of note, even using frequent (e.g. twice daily) and relatively long application times over the course of many weeks, 5% tea tree oil treatment was of limited efficacy in treating acne.

U.S. Patent Publication 2005/0037034 to Rhoades describes a composition for treating comedonal acne associated with acne vulgaris and inflammatory acne. The composition contains an acne treatment agent together with abrasive particles in a base. A method of using the agent is described. The face is buffed or otherwise treated with the agent using, for example, a hand-held vibratory device. The acne treatment agent can be, for example, benzoyl peroxide, salicylic acid, retinol, hydroxyl acid, or tea tree oil.

Increasingly aggressive acne treatment modalities may be used, as shown by the use of oral medications such as isotretinoin, which has significant side effects on the entire body for individuals whose acne cannot be managed by other methods. Simple, effective and safe acne treatments are still lacking.

These acne treatments tend to be harsh, and harsh treatments have traditionally been thought to worsen the symptoms of rosacea. In particular, because skin affected with facial rosacea is easily irritated, the American Academy of Dermatologists (AAD) recommends gentle face washing for patients. The skin should not be rubbed or scrubbed. Even use of a bath puff or washcloth is discouraged as it can be irritating. Use of alcohol, astringents, clove oil, eucalyptus oil, exfoliants, fragrance, peppermint, salicylic acid, toners, and witch hazel has typically been discouraged.

Facial rosacea patients are advised to avoid "trigger" factors. Topical or oral antibiotics may be prescribed, although it is thought that these are effective due to their anti-inflammatory properties, rather than through their antibiotic properties. Laser treatment may be used to reduce the appearance of blood vessels or other redness in the face.

Treatments of facial and ocular rosacea and blepharitis range from simple over-the-counter treatments to treatment from a dermatologist or ophthalmologist, depending on the severity and duration of the symptoms.

Over-the-counter treatments to relieve the symptoms of ocular rosacea and non-rosacea blepharitis include variations of basic washing and massaging routines. In one typical protocol, the eyelids are cleaned and massaged one or more times a day. First a warm, soft compress is applied to the eyelid for 5-10 minutes. This treatment is thought to loosen the lipids in the meibomian glands. Next, the eyelids are cleaned by gently sliding a cotton swab soaked with dilute baby shampoo across the lid margins. Next, the eyelids can be massaged using a finger or swab moving across the eyelid. While there is individual variation, these treatments may generally be performed over of the course of weeks to months to eliminate or reduce the symptoms of blepharitis. Symptoms of blepharitis tend to recur after this type of treatment and require an additional round or rounds of treatment or a different treatment.

In ocular rosacea cases (and in non-rosacea blepharitis cases) did not respond to the wash and massage treatments, other treatments have been tried. Patients have been treated with medications to manage the inflammation (e.g., eye drops containing corticosteroids), topical or oral antibiotics (e.g., doxycycline, gentamicin, tetracycline, azithromycin) to eliminate bacterial infection, surgery, or chemicals to try to control *Demodex* infestation.

U.S. Patent Publication 2007/0203462 to Soroudi and U.S. Patent Publication 2009/0137533 to Adkins describe eyelid treatment kits for improving eyelid hygiene and treating infection and inflammation using antibiotics to eliminate bacterial infection. The kits are meant for treating infection (e.g., blepharitis, meibomitis, acute dacryocystitis, orbital or preseptal cellulitis), treating inflammation (e.g., hordeola, chalazia, or contact dermatitis), treating dry eyes, and/or as post-operative treatment. The kit contains a low dose of an antibiotic (doxycline) and a non-irritating eyelid cleansing composition. Soroudi describes an improved method and materials for use in order to apply heat to the peri-ocular region using a soft, non-abrasive, lint free material such as gauze. The material may contain antibiotics and a cleaner that is gentle to the skin, such as baby shampoo. This material is applied to the eyelid in order to remove bacteria and decrease inflammation.

Other treatments for *Demodex* involve applying volatile liquids such as ether and alcohol to the eyelid to try to kill the mites. However, there are toxicity concerns with use of these chemicals. Additionally, they were not effective at eliminating blepharitis.

Other treatments for blepharitis associated with a *Demodex* infestation involve spreading an ointment containing 1% mercury oxide or 2% metronidazole gel or Pilocarpine at the base of the eyelashes. The purpose is to entrap mites as they emerge from the follicle at night.

Kaoukhov et al., U.S. Patent Publication 2009/0093421, describes compositions for the treatment of ophthalmic pathologies, including ocular rosacea thought to be caused by infestation of *Demodex*, using the anti-parasitic agents avermectin and/or milbemycin. The compositions can be applied directly to the eye, or can be solid forms deployed at the surface of the eye in the form of impregnated pads, snydets, and wipes. Kaoukhov lists various additives that can be included in the compositions, including wetting agents, agents for improving flavor, preservatives, stabilizing agents, agents for regulating moisture, pH-regulating agents; buffers; agents for modifying osmotic pressure; emulsifying agents; agents for increasing viscosity; and antioxidants. The efficacy of this as a topical application is unknown and possible side effects due to the use of avermectin and milbemycin are a concern.

More recently, tea tree oil was tested as a treatment for ocular rosacea. Tea tree oil was originally obtained by steam distillation of the leaves of the *Melaleuca* family of trees, and especially from *Melaleuca alternifolia*, a tree native to Australia. Tea tree oil can be extracted from members of the *Myrtaceae* family, including *Melaleuca alternifolia, Melaleuca linafolia*, and *Melaleuca dissitiflora*. Tea tree oil contains terpenes (pinenes, terpinene, and cymene), cineole, and an alcohol terpinol. It was used as a traditional medicine to prevent and treat infections. It is thought to have antiseptic, antifungal, and antibacterial properties.

Work from Schaffer C G Tseng (Gao et al., "In vitro and in vivo killing of *Demodex* by tea tree oil", *British J of Ophthalmology* (2005) 89:1468-1473; Gao et al., *Cornea* "Clinical treatment of ocular demodecosis by lid scrub with tea tree oil (February 2007): Vol. 26(2); Gao et al. U.S.

Patent Application Publication 2009/0214676; Gao et al. U.S. Patent Application Publication 2009/0061025; Li et al. "Correlation between ocular *Demodex* infestation and serum immunoreactivity to *Bacillus* proteins in patients with facial rosacea", *Ophthalmology* 2010; 117:870-877) describe reagents, tests, and treatment for patients harboring ocular *Demodex*. The authors found that application of tea tree oil, caraway oil, and dill weed oil in vitro would kill *Demodex*. The treatment uses a high concentration of tea tree oil (e.g., 50%) in baby shampoo. The protocol involves cleaning the eyelids and eyelashes with a composition at the doctor's office using a cotton tip wetted in baby shampoo containing 50% tea tree oil. The recommended regimen of six strokes is repeated three times, with a 5-10 minute rest and stroke with a dry cotton tip to remove excess tea tree oil between repeats. The protocol is performed weekly (e.g., for 3-9 weeks) at the clinic. In between clinic visits, the patient continues care at home, generally consisting of daily massages of the eyelids (e.g., for 3-5 minutes) with the fingers using diluted tea tree oil (e.g., 5%) in baby shampoo. The treatment was tolerated by many patients; however others felt eyelid irritation and experienced eyelid spasms during the office tea tree oil treatment. Although the combined treatments rid the eyelids of mites in a majority of the cases, the treatments are inconvenient and costly, requiring weekly visits to the doctor or clinic, as well as additional daily treatments for up to three months. Of particular note, several patients whose symptoms had improved were not entirely rid of the *Demodex* infestations and continued to have symptoms, albeit reduced, of redness, itching, foreign body sensation, dryness, blurry vision, pain, burning sensation and grittiness even after weeks of intensive treatments.

Microdermabrasion is a technique that mechanically ablates skin. It is used on the face, neck or arms to remove dead or damaged skin cells. It speeds the natural process of exfoliation by mechanically removing the uppermost layer of the epidermis. Microdermabrasion makes it easier for skin products to penetrate into the deeper layers of the skin. Epithelialization and collagen production are stimulated. It is used to counteract the effects of acne and photoaging and reduces acne scars, age spots, enlarged pores, fine lines, and the appearance of blemishes, other scars, stretch marks, undesired skin pigmentation, and wrinkles.

Microdermabrasion uses a device to spray fine microcrystals across the skin surface. This treatment causes superficial abrasion that removes a layer of stratum corneum of the skin. Microdermabrasion is currently contraindicated for an individual suffering from rosacea, seborrheic dermatitis, psoriasis, eczema, or vitiligo, and for any use close to the eye or on the eyelid.

SUMMARY OF THE DISCLOSURE

The present invention relates to kits and methods for treating or preventing an eye or eye area condition or for cleansing eye area tissue. The invention also relates to a composition of matter that can be used with the kits and methods. One aspect of the invention provides a method of treating or preventing an eye condition in eye area tissue, such as, e.g., anterior blepharitis, posterior blepharitis, *Demodex* induced blepharitis, conjunctivitis, dry eye, meibomitis, ocular *Demodex* infestation, and ocular rosacea. In some embodiments, the method includes the steps of administering an isoprenoidal essential oil to eye area tissue; chafing eye area tissue with an abrasive, and removing the abrasive. In some embodiments, the step of administering an isoprenoidal essential oil includes administering tea tree oil, such as, e.g., at a concentration of about 0.5% (w/w) to about 4% (w/w) or at a concentration of about 5% (w/w) to about 50% (w/w).

In some embodiments, the step of chafing eye area tissue may include chafing upper eyelid tissue, lower eyelid tissue, eyelid margin tissue, anterior eyelid margin tissue, posterior eyelid margin tissue, or eyelash follicle.

In some embodiments, the step of chafing eye area tissue includes chafing with abrasive particles having a size such as, e.g., from about 1 μm to about 600 μm, from about 25 μm to less than 300 μm, or from about 300 μm to about 600 μm in a longest dimension.

In some embodiments, the step of administering an isoprenoidal essential oil includes administering an abrasive at the same time.

In some embodiments, the abrasive includes abrasive particles and the step of removing the abrasive includes removing the abrasive particles using a material, such as, e.g., a moving gas at a pressure less than atmospheric pressure or an aqueous solution.

Another aspect of the invention provides a kit for treating an eye condition or cleansing an eye area tissue, the kit including an isoprenoidal essential oil for application to eye tissue, an abrasive for chafing eye area tissue, and an instruction for use for treating an eye condition or cleansing an eye area tissue.

In some embodiments, the abrasive includes abrasive particles having a size such as, e.g., from about 1 μm to about 600 μm, from about 25 μm to less than 300 μm, or from about 300 μm to about 600 μm in a longest dimension.

In some embodiments, the isoprenoidal essential oil and the abrasive particles form a mixture.

In some embodiments, the isoprenoidal essential oil includes tea tree oil, such as, e.g., at a concentration of between about 0.5% (w/w) and about 50% (w/w), about 5% (w/w) and about 50% (w/w) or about 0.5% to about 4% (w/w).

In some embodiments, the kit further includes an applicator for applying the isoprenoidal essential oil to an eye tissue and the applicator includes the abrasive.

Yet another aspect of the invention provides a composition of matter including about 0.5% to about 4% isoprenoidal essential oil, such as e.g. tea tree oil, in an ophthalmologically acceptable base and a plurality of abrasive particles.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

A composition of matter according to the disclosure is a novel combination of a microdermabrasive along with a therapeutically effective amount of an isoprenoidal essential oil. The composition may be useful for treatment or prevention of a peri-ocular eye, eyelid, and/or surface ocular condition, disorder, disease, and/or syndrome, and any combination of these conditions, disorders, diseases, and/or syndromes including but not limited to blepharitis (anterior and posterior), *Demodex*-induced blepharitis, ocular *Demodex*, dry eye (dry eye syndrome), meibomitis, meibomian gland dysfunction, pre- and post-operative applications, and ocular rosacea.

The composition may be in ophthalmically acceptable base or may be another base. The composition may be applied to the eyelid, eye margin, and/or area near the eyelid, eyebrow area, or to other areas of the face, or to the neck or body.

The invention further comprises kits and methods for treating and preventing a peri-ocular eye, eyelid, and/or surface ocular condition, disorder, and/or disease, and/or combinations of these conditions, disorders, diseases and/or syndromes, including but not limited to blepharitis (anterior and posterior), *Demodex*-induced blepharitis, ocular *Demodex*, dry eye (dry eye syndrome), conjunctivitis, blepharoconjunctivitis, meibomitis, meibomian gland dysfunction, pre- and post-operative applications, and/or ocular rosacea. The kits, methods, and compositions may also be used to cleanse an eye area that does not have a disease or condition, such as for regular (e.g. daily, weekly, monthly), occasional, or one-time cleansing. The compositions, kits, and methods may remove body oils or other secretions, detritus, dirt, skin cells, or may remove a substance applied to the eye area such as a cosmetic or cosmetic-related product, including but not limited to adhesive, concealer, eye base, eyeliner, eye shadow, mascara. Use of the compositions, kits, and methods described herein may prevent or solve problems related to the eye that may be an area different than the treatment area, such as eye dryness, grittiness, redness associated with contact lens wear, complications or issues related to ophthalmologic or surgical interventions including laser surgery (such as (LASIK, LASEK, PRK).

Figure 1:
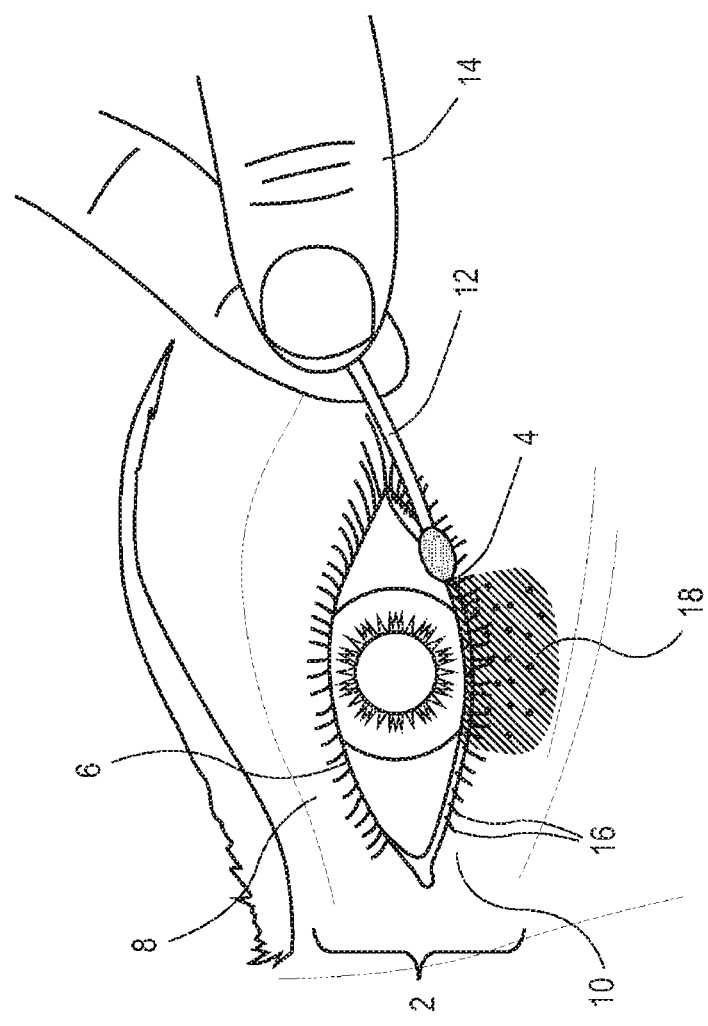
FIG. 1 shows a method of eye treatment using an abrasive according to one aspect of the invention.
Figure 1:
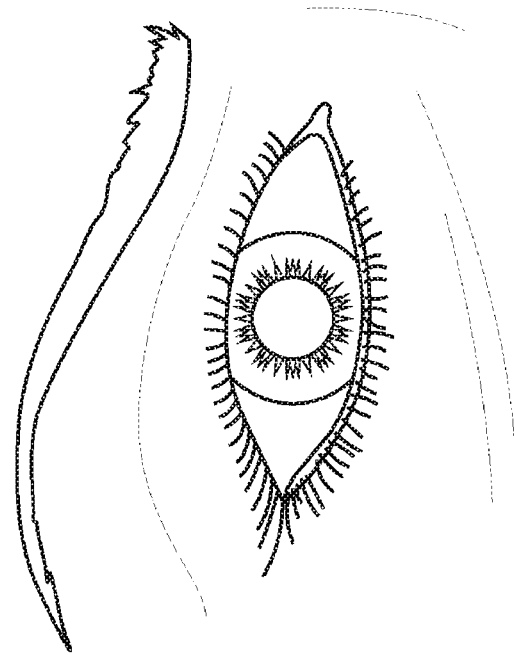

In various embodiments, the microdermabrasive and oil may be applied to the eyelid and/or eye area tissue together, or they may be applied separately. FIG. 1 shows a method of eye treatment using an abrasive according to one aspect of the invention. Eye area tissue 2 is being treated in this example. A finger or device may be used to pull the eyelid at least partially away from the eyeball area to prevent cleaning or treatment material from contacting the eyeball or other sensitive eye areas. Hand-held wand 12 has been used to apply a composition 18 of an abrasive material and isoprenoidal essential oil (e.g. tea tree oil) to lower eyelid margin 4 and lower eyelid 10. Upper eyelid 8 and upper eyelid margin 6 have not been treated. Hand 14 is holding and rubbing wand 4 through mixture 18 to chafe, abrade, and cleanse lower eyelid margin 4, including chafing eyelashes 16. After chafing, the abrasive is removed. The abrasive may be removed by any means, including rinsing with a liquid, treatment with vacuum, and/or wiping (e.g., with a cloth, material, towel, or towelette). Prior to treatment with an abrasive, an eye area tissue may be prepared, such as by washing or rinsing (e.g., with warm water).

Prior eye treatments avoided the use of harsh or abrasive materials near the eye for fear of damaging or irritating the sensitive eye. Abrasive materials, in particular, have been avoided for use near the eye. The novel use in the invention of an abrasive or microabrasive near eye tissue, in combination with an isoprenoidal essential oil, according to one aspect of the disclosure, may allow a lower level of isoprenoidal essential oil to be effective. The use of a lower concentration of oil, in combination with an abrasive or microdermabrasive, may be more effective, safer and less irritating for a patient than is use of a higher amount of oil without an abrasive. In some cases, the treatments may be sufficiently safe to be self-applied by the patient without requiring treatment in a medical setting (e.g., a clinic or physician's office) such as after an initial visit with a physician or other health care provider. In some cases the material may be sufficiently safe to be available over-the-counter and the method used by a patient or individual without requiring a doctor or clinic visit. An option for convenient and inexpensive self-treatment is desirable in any case and may be particularly advantageous for patients who have chronic and/or long-term conditions, and for patients for whom conditions recur after an initially successful treatment regimen. Eye conditions and symptoms may recur in an individual due to a new exposure to a causative agent. For example, Gao et al. (*Cornea*, Vol. 26, No. 2, February 2007:136-143) recommends that a patient being treated for *Demodex* discard make-up and weekly wash their bedding and pillowcases in hot water to prevent re-exposure to *Demodex*. These steps may not be sufficient and may be inconvenient. The compositions, methods, and kits according to the disclosure may be used at home or in a salon or other personal care setting, and may be applied by the individual, a helper, or a facial aesthetic specialist.

While not limiting the method of action of the treatment, it is thought that the treatment acts to remove skin, a layer of skin, skin debris, micro-organisms, eyelashes, oils, and/or other related or unrelated substances. The abrasive particles are thought to work by mechanically agitating the eye area tissue, eyelid, eyelash, and follicle to improve penetration or access of the oil. The treatment may work to agitate or move unwanted material such as *Demodex* eggs, larva or mites and remove them from the eyelash follicle or other part of the eye or eyelid, or to make them accessible to the oil. The dermabrasive may also eliminate organisms by direct killing or damage.

Figure 2:
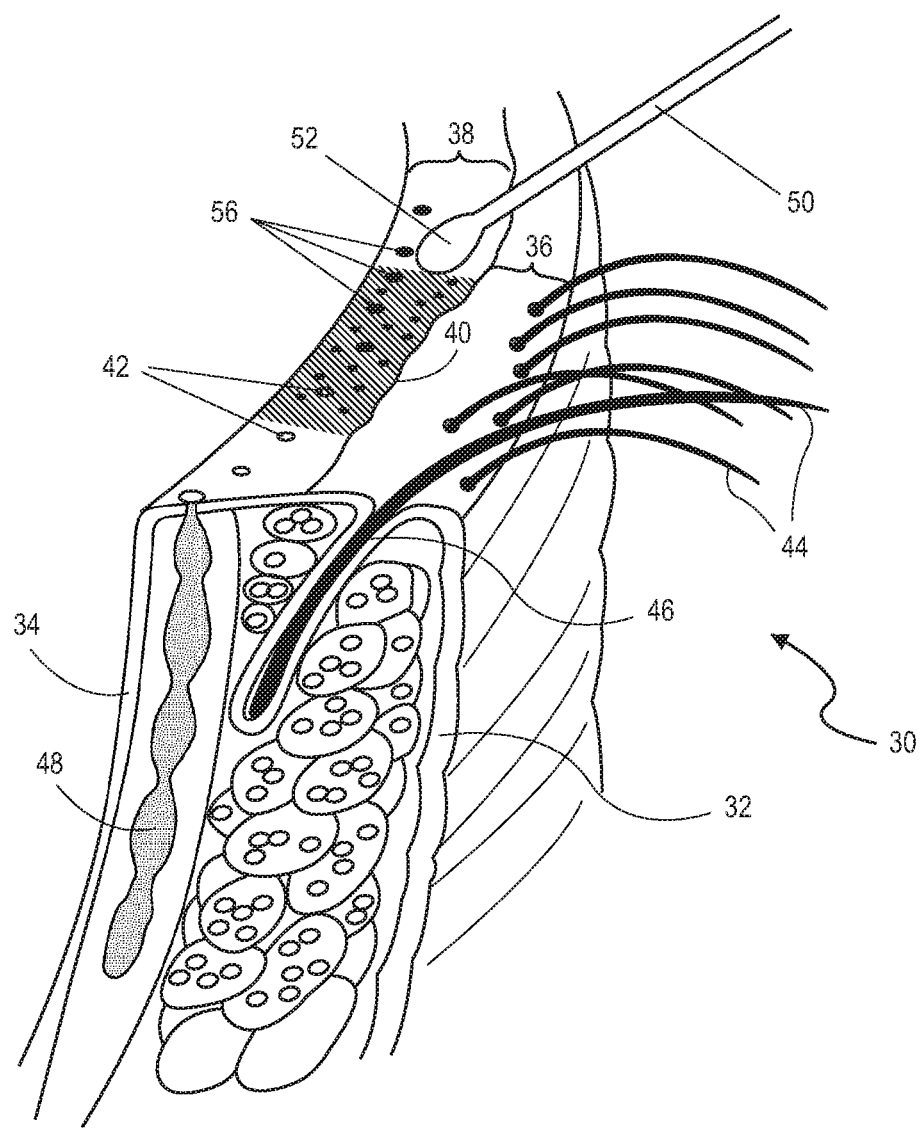
FIG. 2 shows a perspective view of an eyelid margin and a posterior eyelid margin treatment with an abrasive and isoprenoidal essential oil.

FIG. 2 shows a perspective view of an eyelid margin and a posterior eyelid margin treatment with an abrasive and isoprenoidal essential oil. Meibomian glands 56 are blocked, for example by secretions or dirt. Head 52 of wand 50 is chafing posterior eyelid margin 38 on lower eyelid 30 with mixture or composition 57 of abrasive and isoprenoidal essential oil. The treatment is cleaning blocked meibomian glands surface 56 resulting in unblocked or opened meibomian glands 42 and allowing fluid, debris, oils, sebum or micro-biologic material to escape from meibomian glands 48, shown in a cross sectional area of the eyelid in this drawing. Inflammation, irritation, redness and other symptoms and problems may be reduced. Chafing may also or instead be performed along anterior eyelid margin 36, shown on the other side of grey line 40 from the posterior margin, to clean margin surface and eyelash 44. Chafing may also be performed on lower eyelid skin 32. Conjunctiva 34 is free from treatment. Rubbing, chafing, or otherwise agitating posterior eyelid margin, anterior eyelid margin, eyelid skin, and/or other eye area tissue may move eyelash follicle 46 or may move other structures at or below the surface. This agitation along with the chafing may improve or allow flow of body oil, sebum or micro-biologic material out of tissue and may allow penetration of cleansing media or oil, such as isoprenoidal essential oil, into tissues.

The abrasive may include any abrasive particle, powder, or crystal including but not limited to one or more of the following: aluminum oxide (e.g., alumina, aluminum trioxide, corundum powder), barium sulfate, boron nitride, calcium carbonate, cellulose acetate, ceramic, diamond, diatomaceous earth, emerald, ethylene/acric acid copolymer, fibers, garnet, glass, kaolin, lauroyl lysine, lava, magnesium oxide, mica, modified starch, nylon, other metals, other polymers, other silicon dioxides or silicon containing materials, polyethylene, polymethyl methacrylate polypropylene, polystyrene, polytetrafluoroethylene (PTFE), pumice, ruby, sand, sapphire, seashells, sericite, silica, silicon dioxide, silicon carbide, sodium bicarbonate, sodium chloride crystals, starch, silk, talc, topaz, zeolite, or polymer particles. In one embodiment, Kiehl's Epidermal re-texturizing microdermabrasion formulation may be used.

An abrasive particle according to the disclosure may be any shape and have any number of sides. An abrasive particle may be overall diamond (triangle) shaped, elliptical, marquise shaped, octagonal, oval, pear shaped, rectangular, round, squared, or may be combinations or variations (e.g., a rounded square) of these shapes. An abrasive particle may have one surface or may have more than one surface (e.g., sides or faces). An abrasive particle may have 2, 3, 4, 5, 6-10, 11 to 20, 21 to 30, up to 40, up to 50, up to 60, or more than 60 sides. A surface of an abrasive particle may be substantially smooth, regular, textured or irregular. An abrasive particle may have one or more sharp edges or points.

An abrasive particle may be sized from about 1 to about 600 microns (1 μm to 600 μm) across a longest dimension.

Abrasive particles in a group may all be similarly shaped to one another or may be differently shaped from one another. Abrasive particles in a group may all be about the same size, or may range in size. A group of particles may be larger than a minimum or may be smaller than a maximum. A group of abrasive particle may include particles from about 1 to about 15 microns across, about 15 microns to about 25 microns, about 25 microns to about 100 microns, about 100 to about 300 microns, or about 300 to about 600 microns. In one example, a group of abrasive particles may include particles from greater than about 25 microns to less than about 300 microns across. Differently sized and differently shaped particles may be chosen for different reasons. Different sizes and shapes may be chosen for different eye area conditions, different skin types or sensitivities, and/or different methods of application. A particle with a rough surface may be applied using a wand or towelette, while a substantially round particle may be propelled towards the surface under pressure.

An abrasive may include a group of separate particles, or may include a substrate with an abrasive surface or may be any combination or variation. A substrate may have a plurality of abrasive particles connected with (attached to) it to provide an abrasive surface, or it may be a material having a rough textured surface. A rough textured surface may have a pore size on its surface from about 1 to about 15 microns across, about 15 microns to about 25 microns, about 25 microns to about 100 microns, about 100 to about 300 microns, or about 300 to about 600 microns.

The amount and composition of the abrasive in the compound is chosen so as to have the desired effect while minimizing unnecessary abrasion, damage or irritation to the eye region or sensitive peri-ocular region.

The product and method of this disclosure may be used in conjunction with chemical exfoliation, chemical peel, crystal free dermabrasion and/or laser resurfacing.

One or more isoprenoidal essential oil may be included in the composition along with an abrasive. The list of essential oils includes but is not limited to those described in U.S. Patent Publication 2009/0214676 to Gao et al., which is incorporated herein by reference. 1,4-cineole, 1,8-cineole, (4R)-limonene 1,2-epoxide, 3-isopropoxyphthalide, 3-propoxyphthalide, 6-terpinolene, 7-methyl-3-methylideneocta-1,6-diene (myrcene), acetaldehyde, alpha-pinene, alpha-terpinene, alpha-terpineol, alpha-thugene, caraway oil, cardinene, (+)-carvone, (+)-cis-limonene 1,2 epoxide, cuminic aldehyde, d-carvone, dill seed oil, dill weed oil, dipentene, dipentene (+/−)=limonene, eucalyptol, furfurol, gamma-terpinene, 1-carvone, (+)-ledene, (+)-limonene, (R)-(−)carvone, (R)-(+)-limonene, myrcene, para-cimene, (S)-(+)-carvone hydrate, Tea tree oil (Oil of Melaleuca), terpinen-4-ol, and/or variations and/or pharmaceutically accepted salts thereof may be added. The concentration of the oil(s) in the formulation may be any safe and effective amount. Higher concentrations may be more effective but may be administered by a health care professional to ensure safety. The oil may be added to the composition at concentrations from less than about 1% (w/w) and up to about 50% (w/w). About 50% to about 60%, about 70%, about 80%, about 90% or about 95-99% oil may be added to the composition. The oil may be added at about 0.5%, about 1%, about 2%, about 3%, about 4% or about 5% to the composition. For example, an over-the-counter formulation may contain oil(s) at a concentration of about 0.5% to about 4% (e.g. about 0.5% to 4.5%). In another example, a formulation (e.g., available by prescription, from a physician or for use in a physician's office) may contain from about 5% up to about 50% or more oil. In another example, a formulation may contain from about 5% up to about 10%, about 20%, about 30%, about 40%, or about 50%. Any changes to tree oil composition and manufacture as covered by ISO standard 4730, including updates to the standard, are included. The tea tree oil may be obtained by steam distillation from a *Melaleuca* tree, or may be obtained from a manufactured source containing terpinen-4-ol. Any form or variation of tea tree oil may be added.

The oil and microabrasive may be combined into any form, including but not limited to colloid, cream, gel, emulsion, liquid, ointment, lotion, paste, semi-liquid, solution, and solid.

Other constituents may be added, either singularly or in combination, including but not limited to acne treatment agent, alcohol, animal extract, anti-oxidant agent, anti-parasitic agent, antiseptic agent, anti-bacterial agent, ash, astringent, balm, binder, bleaching agents, collagen stimulating agent, colorants, desquamation additives, drying agent, EDTA, emollient, flower or flower extract, free radical scavenger, fruit or fruit extract, hair growth regulators, herbs or herb extract, honey, humectant, hydration agent, lubricant, lubricity agent, moisturizer, numbing agent, nuts or nut extract, oil, other anti-microbial agents, other cleaner, other essential oils, other microcidal agents, other plant extract, peel agents, peptides, pH buffering agent, protein, shampoo, skin conditioner, soap, sunscreen, toner, tree or tree extract, unguent, vegetable extract, viscosity control agent, vitamin, vitamin analog (e.g., allantion, Aloe vera, alpha hydroxy acids, alphanoic acid, Amazonian White Clay, benzoyl and other peroxides, carotenoids, ceramide, coenzyme Q10, collagen, copper, copper peptide, cortisone, elastin, glycerin, glycolic acid, green tea extract, hyaluronic acid, hydrolipids, hydroquinone, hydroxyl acid, ivermectin, lactic acid, lanolin, magnesium, mineral oil, niacin, non-silicone oil (hydrocarbon oil, esters, ethers), oatmeal, panthenol, phospholipids, polyethylene glycol (PEG) or modified PEG, retinoids, retinol, retinyl propionate, salicylic acid, sea algaenates, Shea butter, silicone oil, sodium chloride, sodium hyaluronate, triclosan, urea, Vitamin B, Vitamin C (ascorbate), Vitamin E (tocopherol), water, willow herb, willow weed, witch hazel, zinc oxide.

Figure 3:
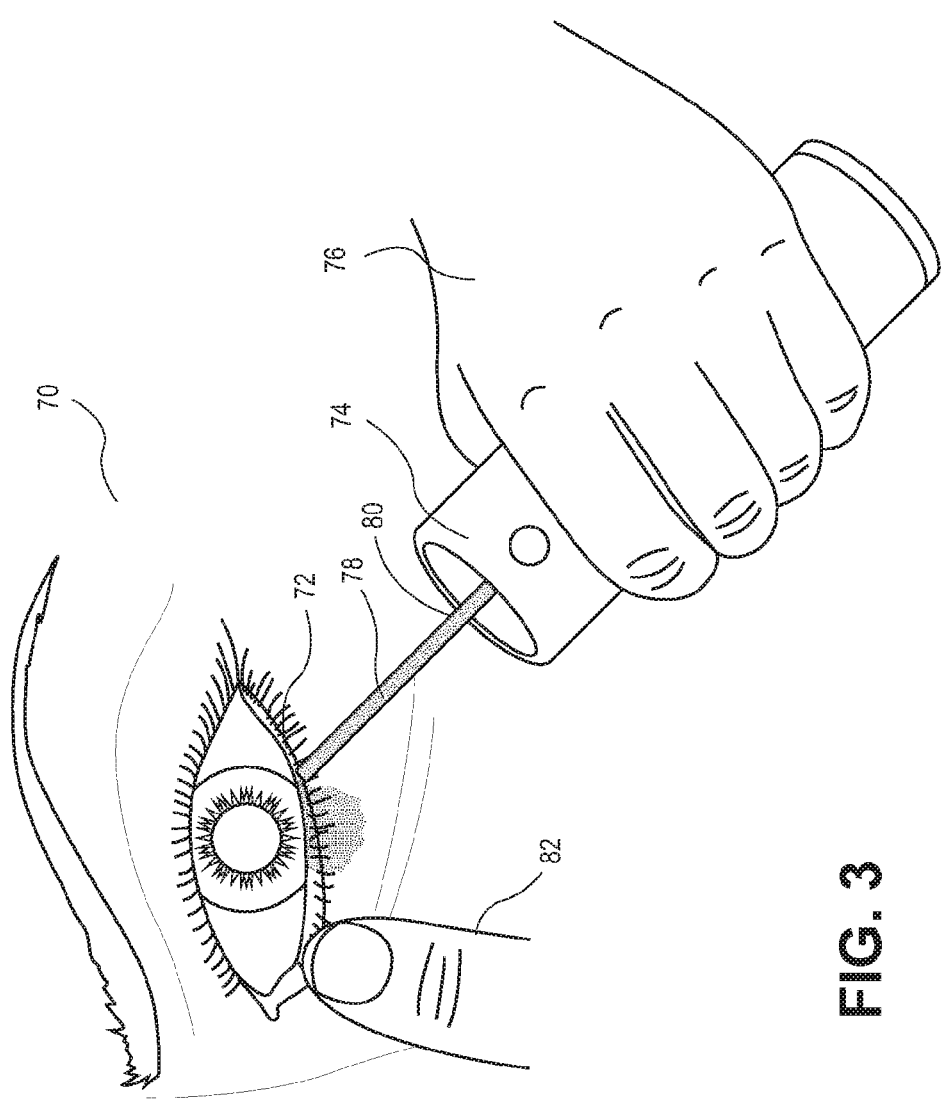
FIG. 3 shows hand-held applicator dispensing mixture of an abrasive and an isoprenoidal essential oil to an eye area tissue and chafing eye area tissue with the abrasive.

A composition according to the disclosure may be applied as shown in FIG. 3. FIG. 3 shows hand-held device 74 dispensing mixture 78 of an abrasive and an isoprenoidal essential oil from applicator 80 to eye area tissue 70 including eyelid margin tissue and eyelid tissue. The device is being used by an individual 76 to chafe eyelid margin tissue 72 with the mixture. The applicator may rotate, rub, vibrate, or otherwise move to aid in the chafing process. The individual's finger 82 holds eyelid margin 72 away from the eyeball to prevent the mixture and applicator from contacting the eyeball.

A composition or material for use may be dispensed in any way (e.g., from an applicator/device/wand, a bottle, a jar, a package (e.g., an individual package), a pump (pump bottle), a tube, or a tub. The material may be dispensed to any appropriate material, such as an applicator/device/wand, a finger, an individual wipe, or a towelette. A material may be dispensed directly to a tissue, such as an eye area tissue, from a dispenser.

The invention includes methods of topically administering a composition containing an oil and abrasive to eye area tissue including to an eyelid and eye margin.

Figure 4:
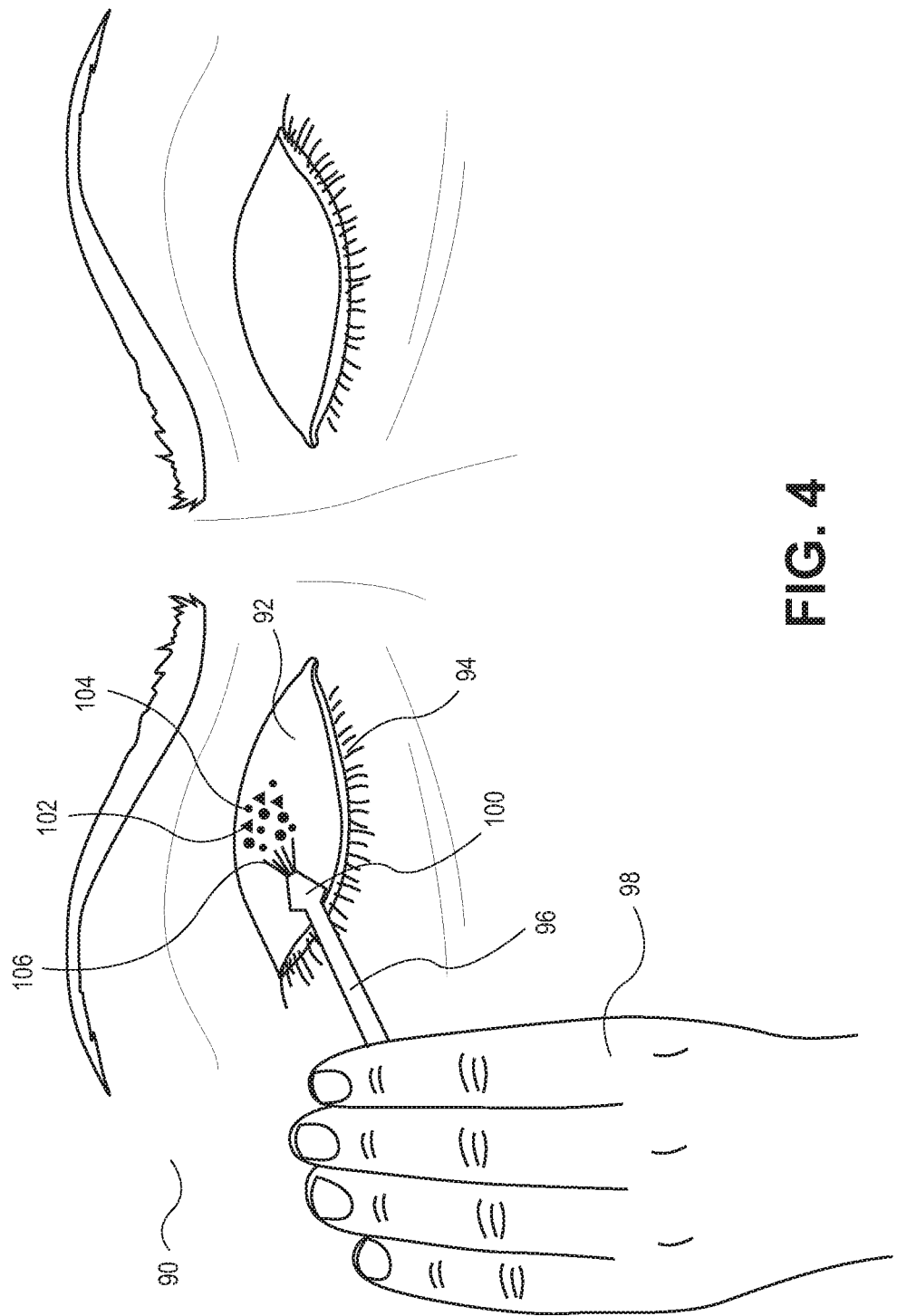
FIG. 4 shows application of an abrasive composition to an eyelid using a pressurized liquid.

FIG. 4 shows a physician, technician or aesthetician chafing an abrasive 102 and isoprenoidal essential oil 104 on upper eyelid 92 using pressurized liquid 106. A mixture containing the oil and microdermabrasive is propelled onto eyelid 92, eyelash 94, or other eye area tissue 90 using applicator 96 as held by a physician or aesthetician 98. Head 100 of applicator 96 may be any shape or size to allow application and/or cause chafing. For example, a smaller head may be used for eye area tissue around the eyelashes and a relatively larger head may be used over the bulk of the eye lid or eye area (or other face, neck, or body) tissue. The composition may be propelled in any way, such as using a compressed gas or compressed liquid. The composition may be a liquid or may be in the form of an aerosol. The composition may be under pressure before application or may be pressurized during application. A vacuum may be used to draw the mixture across the eyelid.

Any device may be used, such as those described in US 2002/0169461 to Simon et al. or US 2004/0092959 to Bernaz.

Figure 5:
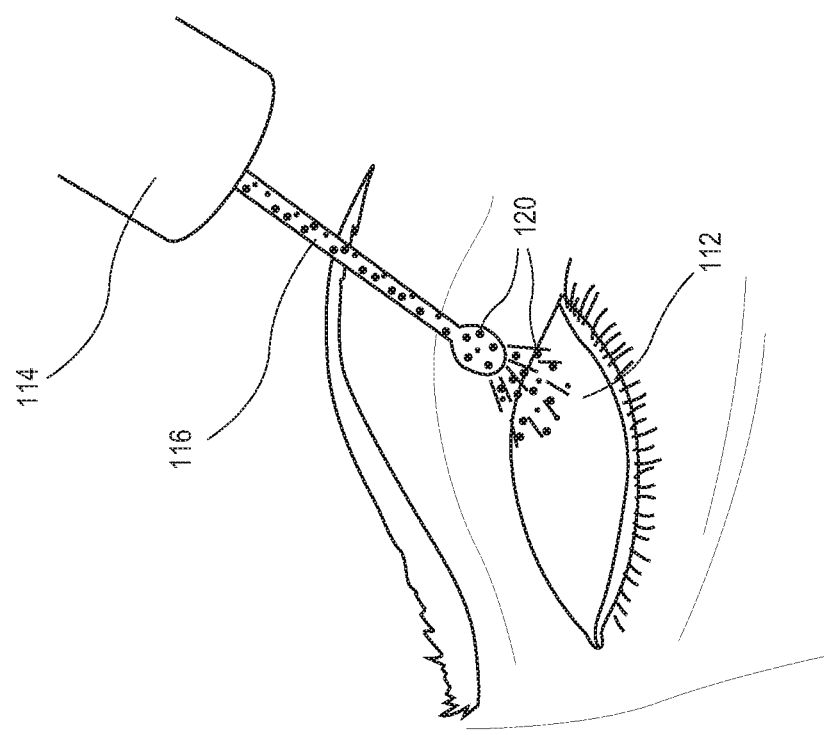
FIG. 5 shows an abrasive being removed from eye area tissue using a vacuum source.

Excess, used, or otherwise unwanted abrasive may be removed by any means, such as using a towel, a wand, or a wipe. A device may be used to remove excess, used, or otherwise unwanted abrasive mixture, such as by using liquid or vacuum. FIG. 5 shows vacuum source 114 connected with vacuum tubing or conduit 116 removing used abrasive mixture 120 from eyelid 112. A low pressure source may be used to remove abrasive and/or tea tree oil from any part of the body, including from eye area tissue 110.

In another embodiment, essential oil is applied to the eyelid and/or surrounding area using a device, and chafing may be performed with an abrasive pad.

In another embodiment, a high pressure water may be abrasive. Isoprenoid oil may be added to a high pressure water stream using any device, such as described in US 2009/0138026 to Wu.

The compound containing the oil and microdermabrasive may be massaged into the eyelid. Massage may be performed using the fingers.

In other embodiments, the composition may be applied to the eyelid and/or eyelash using part of the body, such as a knuckle or finger, or a material (e.g., a pad, sponge, brush, sponge, or swab containing an applicator such as cotton, polyester, rayon, or other material). In another embodiment, the composition may be applied using a microdermabrasion device.

In one embodiment, the composition is dispensed from a tube and applied to the eye margin using a finger. The eyelid may be pulled away from the eye to prevent the composition from contacting the eyeball. The composition may be carefully massaged into the eye margin, with care taken to avoid contact with the eyeball and other sensitive eye tissue.

In another embodiment, the compound may be coated on the eyelid in a manner similar to the manner in which eye liner makeup or mascara is applied.

In another embodiment, the compound may be applied by squeezing a therapeutic amount of material out of a squeezable tube or bottle.

Any of these methods of applying the compound may be combined with any other method.

The amount of composition applied and the method of applying it may be chosen so as to have the desired effect while minimizing unnecessary abrasion, damage or irritation to the eye region.

A kit for treating or preventing a peri-ocular eye, eyelid, and/or surface ocular condition, disorder, disease, and/or syndrome, and any combination of these conditions, disorders, diseases, and/or syndromes including but not limited to blepharitis (anterior and posterior), *Demodex*-induced blepharitis, ocular *Demodex*, dry eye (dry eye syndrome), meibomitis, meibomian gland dysfunction, pre- and post-operative applications, and rosacea or for cleaning eye area tissue may include one or more of any of the items listed in the disclosure. Additional items may also be included.

Figure 6:
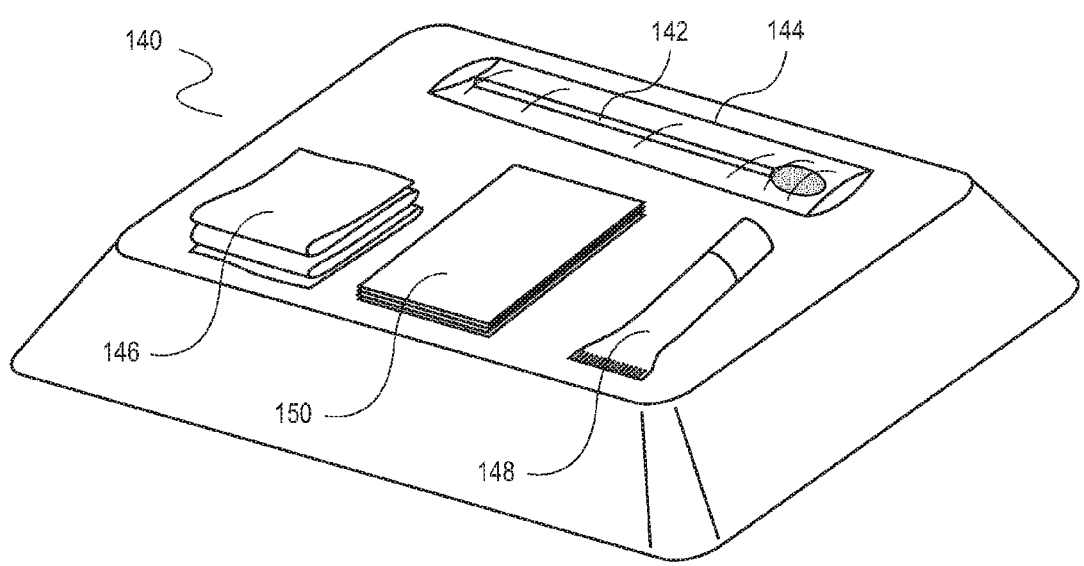
FIG. 6 shows a kit for eye treatment or eye cleansing according to one aspect of the invention.

FIG. 6 shows kit 140. The kit has applicator 142 in sterile package 144. Tube 148 contains a mixture of an isoprenoidal essential oil and abrasive in an ophthalmologically acceptable base for application to eye area tissue. An ophthalmologically acceptable base is a material that can be placed into a mammalian eye without causing any substantial harm or damage to the eye. Towelette 146 for cleaning or removing abrasive and any instruction for use 150 are included. A kit may have all of these items or may have some of these items or may instead have other items described herein.

For example, the kit may include the following or combinations of the following: a container comprising microdermabrasive combined with an isoprenoid essential oil such as tea tree oil, a container comprising an isoprenoid essential oil such as tea tree oil, a container comprising a microdermabrasive, a dispenser configured to dispense isoprenoid oil, a microdermabrasive, or a combination of the isoprenoid oil and microdermabrasive, one or more containers comprising a lubricant, a cleansing agent, a shampoo, an anesthetic agent, a topical antiseptic, a topical antibiotic, an oral antibiotic or other oral supplement, a microdermabrasive device, an applicator (e.g., pad or swab), a set of directions for how to use the kit or scrub, and/or one or more disposable towels. An isoprenoidal essential oils and abrasives may be included in the kit. Any item in a kit may be sterile, may be in a sterile package, or may not be sterile or not be in a sterile package.

A kit may include an instruction for use, such as an instruction for chafing eye area tissue, for example by using an abrasive applicator, using an abrasive device, or adding an abrasive material and adding an isoprenoidal essential oil. An instruction for use may include an instruction for mixing an abrasive and oil (and other materials) to produce a mixture or composition for treating peri-ocular eye and eyelid conditions, disorders and/or disease, including but not limited to blepharitis (anterior and posterior), *Demodex*-induced blepharitis, ocular *Demodex*, dry eye, meibomitis, pre- and post-operative applications, and rosacea. The directions may describe cleansing eye area tissue, including cleansing an eyelid, eye margin, and eyelash follicle with any of the materials and using any of the methods described herein.

A kit may be configured for use by an individual (such as for use at home or for use elsewhere (e.g., it may be portable) or it may be configured for use in a doctor's office, clinic, hospital or salon.

Alternatively, the oil and microabrasive components may be stored separately, and applied separately to the eyelid. An abrasive may be used to apply an oil and chafe an eye tissue. An applicator may comprise an abrasive, such as an abrasive surface or an abrasive end that may be used to chafe or abrade eye tissue. They may be applied at the same time on the eye area tissue or eyelid, mixed together, and the eyelid scrubbed. Alternatively, either one may be applied, the eyelid scrubbed and optionally rinsed, and then the other component may be applied. The eyelid may be scrubbed. The process may be repeated.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A method of treating anterior blepharitis, posterior blepharitis, *Demodex* induced blepharitis, conjunctivitis, dry eye, meibomitis, ocular *Demodex* infestation, or ocular rosacea in eye area tissue comprising:
   administering an effective amount of isoprenoidal essential oil to the eye area tissue; and
   chafing the eye area tissue with an effective amount of abrasive particles.

2. The method of claim 1 wherein the isoprenoidal essential oil comprises tea tree oil.

3. The method of claim 2 wherein the concentration of tea tree oil is about 0.5% (w/w) to about 4% (w/w).

4. The method of claim 2 about the concentration of tea tree oil is about 5% (w/w) to about 50% (w/w).

5. The method of claim 1 wherein chafing the eye area tissue comprises chafing a tissue selected from the group consisting of: upper eyelid tissue, lower eyelid tissue, eyelid margin tissue, anterior eyelid margin tissue, posterior eyelid margin tissue, and eyelash follicle.

6. The method of claim 1 wherein the abrasive particles have a size from about 1 µm to about 600 µm in a longest dimension.

7. The method of claim 6 wherein the abrasive particles have a size from about 25 µm to less than 300 µm in a longest dimension.

8. The method of claim 6 wherein the abrasive particles have a size from 300 µm to about 600 µm in a longest dimension.

9. The method of claim 1 wherein chafing the eye area tissue comprises performing a motion selected from the group consisting of rubbing and vibrating the eye area tissue.

10. The method of claim 1 wherein administering the isoprenoidal essential oil further comprises administering the abrasive particles at the same time.

11. The method of claim 10 wherein the administering step comprises administering the isoprenoidal oil and the abrasive particles in an ophthalmologically acceptable base to the eye area tissue.

12. The method of claim 11 wherein the isoprenoidal oil comprises tea tree oil.

13. The method of claim 1 further comprising removing the abrasive particles.

14. The method of claim 1 wherein the method further comprises removing the abrasive particles using a material selected from the group consisting of a moving gas at a pressure less than atmospheric pressure and an aqueous solution.

15. A method of treating anterior blepharitis, posterior blepharitis, *Demodex* induced blepharitis, conjunctivitis, dry eye, meibomitis, ocular *Demodex* infestation, or ocular rosacea in eye area tissue comprising:
   administering an effective amount of tea tree oil to the eye area tissue; and
   chafing the eye area tissue with an effective amount of abrasive particles.

16. The method of claim 15 wherein the administering step comprises administering the tea tree oil and the abrasive particles in an ophthalmologically acceptable base to the eye area tissue.

17. The method of claim 15 further comprising removing the abrasive particles.

18. The method of claim 17 wherein the removing step comprises removing the abrasive particles using a material selected from the group consisting of a moving gas at a pressure less than atmospheric pressure and an aqueous solution.

19. The method of claim 15 wherein the abrasive particles have a size from about 1 µm to about 600 µm in a longest dimension.

20. The method of claim 15 wherein the abrasive particles have a size from about 25 µm to less than 300 µm in a longest dimension.

21. The method of claim 15 wherein the abrasive particles have a size from 300 µm to about 600 µm in a longest dimension.

* * * * *